United States Patent [19]

Worley, deceased et al.

[11] 4,441,510
[45] Apr. 10, 1984

[54] METHOD AND APPARATUS FOR FETAL PH SCALP STUDIES

[76] Inventors: Michael W. Worley, deceased, late of Salt Lake City, Utah; by Shauna Worley, legal representative, 2021 Hollywood Ave., Salt Lake City, Utah 84101

[21] Appl. No.: 172,254

[22] Filed: Jul. 25, 1980

[51] Int. Cl.³ .............................................. G01N 33/16
[52] U.S. Cl. .................................... 128/763; 128/760; 604/903
[58] Field of Search ................ 128/DIG. 28, 763, 760

[56] References Cited

U.S. PATENT DOCUMENTS 4,214,874  7/1980  White .............................. 128/763 X Primary Examiner—Kyle L. Howell
Assistant Examiner—Nancy A. B. Swisher
Attorney, Agent, or Firm—B. Deon Criddle

[57] ABSTRACT

Apparatus for use in obtaining and processing for analysis blood scalp samples during fetal monitoring. A hollow tube having a blood collection assembly at one end is provided. The blood collection assembly comprises a capillary tube, capped at one end, coated with heparin on the inside, a metal flea inside the tube and held positioned by a magnet outside the tube and means for positioning the magnet until mixing of the blood and heparin is desired.

3 Claims, 6 Drawing Figures

METHOD AND APPARATUS FOR FETAL PH SCALP STUDIES

BRIEF DESCRIPTION OF THE INVENTION

1. Field of the Invention

This invention relates to equipment used in blood scalp sampling of a fetus immediately prior to birth. Analysis of the blood of the fetus serves to monitor stress and whether the placenta is functioning properly. While useful in connection with almost all births, it has proven very particularly useful and important in the monitoring of high risk patients.

2. Prior Art

In the past blood scalp sampling has been accomplished using a vaginal cone through which the attending physician has inserted a wand with a scalpel blade to make an incision and a long capillary tube that is then inserted to obtain a blood specimen. The long flexible capillary tubes are easily broken, and because of their flexibility are difficult to use. This is particularly true if the vaginal cone moves as the physician inserts the long capillary tube to obtain the specimen and as the specimen is transferred from the tube to another vessel for analysis.

SUMMARY OF THE INVENTION

Objects of the Invention

Principal objects of the present invention are to provide a blood collection assembly that is easy to use for fetal monitoring; that reduces the danger of tube breakage commonly associated with such procedures in the past; and that provides for easy analysis of the blood sample obtained.

Features of the Invention

Principal features of the invention include a long handled, substantially rigid, wand-type scalpel for use in making an incision; a tubular, substantially rigid, long-handle carried aspirator needle inserted through the capped end a short length of capillary tubing. The interior of the capillary tubing is coated with heparin. A small piece of metal, i.e. a metal flea, is positioned inside the tube prior to obtaining a blood sample and a magnet is placed around the tube to hold the flea in place. The magnet is positioned between the end cap of the tubing and a yieldable collar on the tubing.

Because of the rigidity of the long-handled aspirator needle and the relatively short length of the capillary tube connected to the long handle by the needle, little, if any, bending of the assembled structure occurs as a blood sample is obtained or when sample is handled during analysis.

Since the metal flea is pre-inserted and is held in place by the magnet the capillary tube is not subject to being broken, as in the past, by a person wearing sterile rubber gloves trying to insert such a flea to cause a mixing action between the blood sample and the heparin coating on the inside of the capillary tube. Furthermore, movement of the magnet, along the exterior of the short capillary tube after the magnet is released to move on the tube insures a positive movement of the flea inside the tube and thorough mixing of the blood and heparin without the need for shaking or other movement of the tube that may break the tube.

Additional objects and features will become apparent from the following detailed description, taken together with the accompanying drawing.

THE DRAWING

In the drawing:

FIG. 1 is a perspective view of a tubular long-handled aspirator needle of the invention;

FIG. 2, a cross-section view, taken on the line 2—2 of FIG. 1;

FIG. 3, a perspective view of a long-handled, wand-type scalpel usable in practicing the method of the invention;

FIG. 4, a side elevation view of a short capillary tube having a surrounding magnet secured to be substantially immovable thereon;

FIG. 5, a view like that of FIG. 4, but with the magnet released for movement on the tube and broken away to show a metal flea inside the tube; and FIG. 6, a pictorial view of a fetus, and the assembled components of FIGS. 1 and 4 arranged to be inserted through a vaginal cone to obtain a sample of blood from the scalp of the fetus.

DETAILED DESCRIPTION

Figure 1:
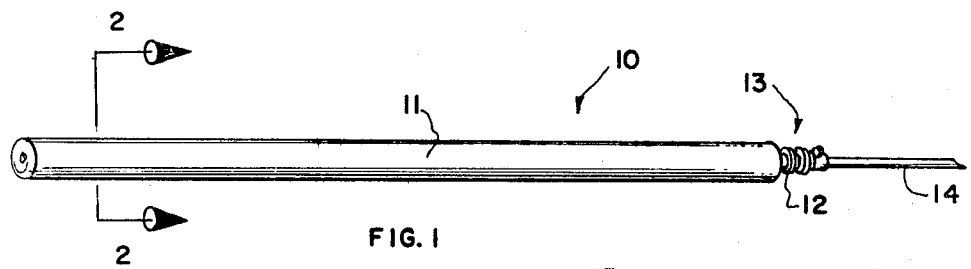
Figure 3:
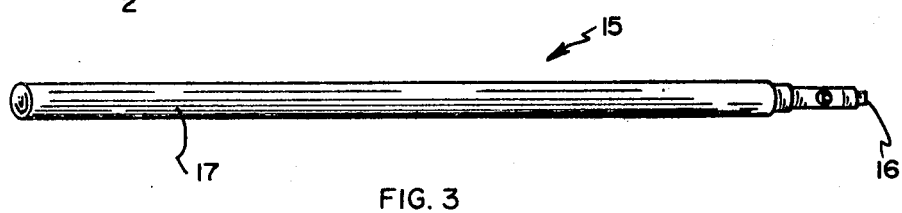
Figure 4:
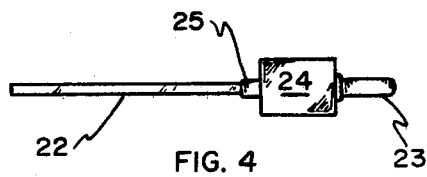

Referring now to the drawing:

In the illustrated preferred embodiment of the invention, the individual items of equipment necessary to practice the method of the invention are shown in FIGS. 1-5.

FIG. 1 shows an aspirator needle assembly 10 used to collect blood from the scalp of a fetus. As shown, the assembly 10 includes a long, substantially rigid, tubular handle 11, one end of which has the blunt end 12 of an aspirator needle set 13 inserted therein. The aspirator needle set is fixed to the end of the handle and the pointed end 14 of the set projects therefrom.

Figure 2:

As best seen in FIG. 2, a conventional surgical scalpel 15 having a blade 16 at one end of a long (approximately ten inch) substantially rigid handle 17, is used to make an incision during an initial step of the method of the invention.

In practicing the method, a vaginal cone 18 is inserted through the vagina of an expectant mother and into contact with the scalp of the fetus. While vaginal cones have been used in the past, a preferred cone for use with the invention permits a slight negative air pressure to be induced through tube 20 to the interior of a fetus engaging flexible smaller end 21 of the vaginal cone. The positive pressure acting on the outside of the smaller end then holds the cone in place on the scalp.

After the cone 18 has been inserted and positioned, the blade end of the surgical scalpel is inserted through the cone to make a small incision in the scalp. The doctor using the scalpel can readily examine the scalp surface through the cone to make the incision precisely where desired.

In the past, it has been common, after the incision is made, to use a long, (approximately ten inch) glass capillary tube to collect a blood sample at the incision. Such sample has then generally been transferred to a test vessel and been heparinized before being analyzed. The long capillary tubes are rather flexible and bend during use, thus making it difficult to position the tip to obtain a sample. The long slender tubes have been subject to frequent breakage while being used to obtain a sample, while the sample is being stored, or the sample is transferred from the tube to a sample analysis vessel.

With the sample collection apparatus of the invention, however, only a short (approximately four inch) capillary tube section is used. The capillary tube used is shown best in FIGS. 4 and 5 at 22. A cap 23 of rubber or other similar material closes one end of the tube and a magnet 24 encircles a portion of the tube to be held in place between the cap 23 and a flexible sleeve 25 serves as a yieldable collar. The interior of the tube 22 is coated with heparin, in customary fashion, and a small piece of metal, i.e. a metal "flea" 26 is placed in the tube and is held in position within the surrounding magnet 24.

Figure 5:
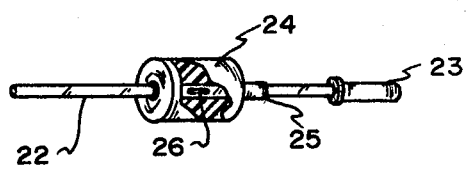

As best seen in FIG. 5, the diameter of the bore of the magnet is such that with carefully applied pressure the magnet will slip over the sleeve 25 and will then be free to travel back and forth along the length of the tube from sleeve 25 to the end of the tube. Naturally, the flea 26 moves with the magnet during such travel, and the movement of the flea in the tube thoroughly mixes the blood sample and the heparin coating from the interior of the tube.

In obtaining a blood sample using the apparatus of the invention, the handle 11 is grasped and the pointed end 14 of the needle is inserted through the cap 23 and fully into the tube 22 while the magnet 24 is held captured between end cover 23 and sleeve 25. The short capillary tube thus forms an extension of the substantially rigid handle 11 and since little bending occurs in the short capillary tube the assembled blood collection apparatus is essentially rigid for its entire length.

Figure 6:
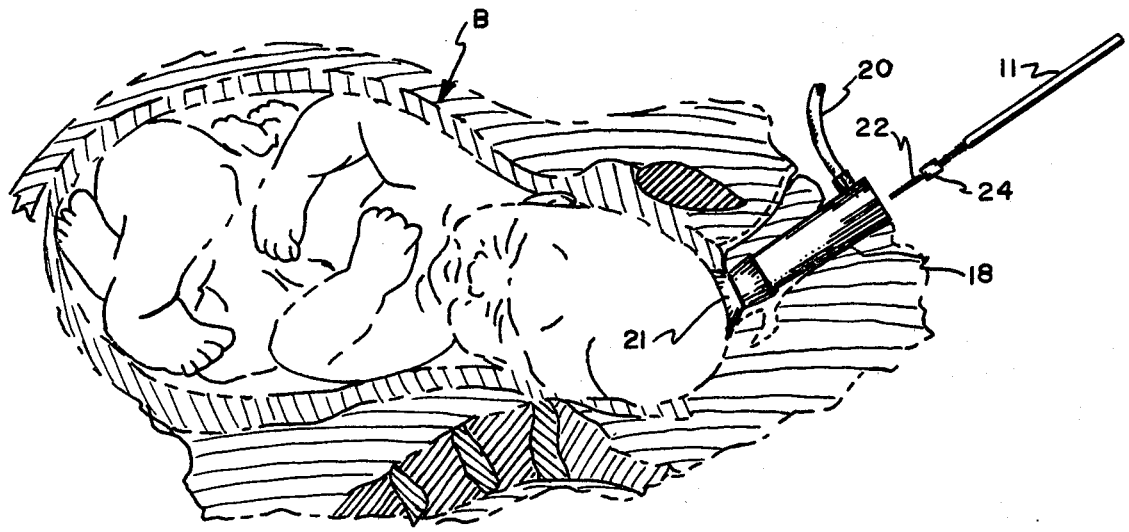

As shown best in FIG. 6, the vaginal cone 18 is inserted through the vagina to position end 21 thereof against the scalp of the baby B. Thereafter, a negative pressure is introduced into line 20 to hold the end 21 in place against the scalp. The long handled scalpel 15 is inserted through the vaginal cone to make an incision and then is discarded. The assembled blood collection apparatus, comprising the handle 11 and needle 14 inserted into the short capillary tube 22 is used to collect blood from the incision. This is done by holding the handle 11 to insert the free end of tube 22 through the vaginal cone to the incision so that blood will move by capillary attraction into the tube. The passages through the needle and hollow handle 11, to atmosphere, permit air to escape and insure proper capillary action as the capillary tube is filled. The blood collection apparatus is withdrawn from the vaginal cone and the cone may be removed or left in place for future sampling, as may be determined to be necessary or desirable.

After the blood collection apparatus has been withdrawn the handle 11 and needle 14 are separated from the capillary tube. Pressure is then applied to the magnet to move it over sleeve 25. The magnet is then reciprocated along the tube 22 to move the flea therein and to mix the blood and heparin, as has been explained. The heparinized blood can be safely stored in the capillary tube 22 for several hours before it is tested or it can be tested immediately following sampling. The cap 23 keeps the blood from being discharged from the capped end of tube 22 and a negative pressure in the tube at the cap will keep the blood from being lost from the other end of the tube.

Although a preferred embodiment of the invention has been illustrated and described, it will be recognized that other embodiments are possible without departing from the subject matter of the claims, which claims are regarded as defining the invention.

What is claimed is:

1. Apparatus for obtaining blood for fetal pH scalp studies comprising
   an elongate, substantially rigid, tubular handle;
   an aspirator needle having its pointed end projecting from one end of the tubular handle and its other end opening into the handle;
   a capillary tube having a self-sealing cap on one end thereof through which the pointed end of the needle is inserted to extend into the capillary tube, and heparin on the inner wall thereof, and a metal flea therein;
   a yieldable collar surrounding the capillary tube a spaced distance from the self sealing cap and adjacent the one end of the capillary tube; and
   a magnet encircling the capillary tube between the self-sealing cap and the yieldable collar, said magnet having a bore dimensioned to slide over the collar upon application of sufficient force to said magnet and deformation of the collar the yieldable collar being spaced from the self-sealing cap a distance just greater than the length of the magnet along the capillary tube.

2. Apparatus as in claim 1, wherein the cap and the collar are of rubber.

3. Apparatus for use in obtaining blood samples comprising
   a capillary tube having a self-sealing cap on one end thereof through which the pointed end of a needle is adapted to be inserted;
   a coating of heparin on the inner wall of the capillary tube;
   a metal flea in said capillary tube;
   a yieldable collar surrounding the capillary tube a spaced distance from the self-sealing cap and adjacent the one end of the capillary tube; and
   a magnet encircling the capillary tube between the self-sealing cap and the yieldable collar, said magnet having a bore dimensioned to slide over the collar upon application of sufficient force to said magnet and deformation of the collar the yieldable collar being spaced from the self-sealing cap a distance just greater than the length of the magnet along the capillary tube.

* * * * *